US00PP11015P

United States Patent [19]

Duncan

[11] Patent Number: Plant 11,015

[45] Date of Patent: Jul. 27, 1999

[54] EUONYMUS FORTUNEI PLANT NAMED 'DUNCANATA VARIEGATED VEGETA'

[75] Inventor: Roy L. Duncan, Battle Creek, Mich.

[73] Assignee: Roy L. Duncan and Arlene G. Duncan Trustees of the Roy L. Duncan and Arlene G. Duncan Living Trust, Battle Creek, Mich.

[21] Appl. No.: 08/992,171

[22] Filed: Dec. 17, 1997

[51] Int. Cl.[6] ..... A01H 5/00

[52] U.S. Cl. ..... Plt./246

[58] Field of Search ..... Plt./63, 246

*Primary Examiner*—Howard J. Locker
*Assistant Examiner*—Anne Marie Grünberg
*Attorney, Agent, or Firm*—Burns, Doane, Swecker & Mathis, L.L.P.

[57] ABSTRACT

This new cultivar of *Euonymus fortunei* originated as a branch sport of the all-green 'Vegeta' variety (non-patented in the United States). The new cultivar combines the relatively large and broad leaf characteristics as well as the hardiness of the parent 'Vegeta' variety with attractive variegated foliage. Plants of the new cultivar have generally wide and irregular whitish-cream leaf margins that commonly cover approximately 20 to 60 percent of the leaf area. This distinctive margin coloration surrounds and occasionally penetrates the leaf centers that are of marbled green and deep forest green. This atypical leaf character gives the new cultivar a characteristically lush and luminous, and artistic appearance. The appearance of the new cultivar is further enhanced by the presence of distinctive whitish stems, and occasionally by a few pearl-like whitish capsules which expose orange-red arils upon dehiscence. The new cultivar exhibits substantially the same form and growth habit as the 'Vegeta' variety with the exception that it is slower growing and somewhat smaller in size for a given age. This renders it particularly well suited for growing as a clinging and climbing vine to cover surfaces such as a masonry wall, fence, trellis or tree; as a mounding groundcover; or as a low-spreading shrub when an older plant is selected.

4 Drawing Sheets

SUMMARY OF THE INVENTION

The new cultivar was discovered and selected by me in 1963 in Battle Creek, Mich. from within a planting of the 'Vegeta' variety of *Euonymus fortunei* which was climbing and providing cover for a wall. Such 'Vegeta' variety typically exhibits all green foliage. One particular branch of a plant of the 'Vegeta' variety was found and collected by me due to its remarkably different leaf and stem coloration from the rest of the plant. This mutation or sport was of unknown causation. Had this distinctive branch not been discovered, studied and preserved by me, it would have been lost to mankind. It has been found that the new cultivar of the present invention exhibits the following characteristics:

(a) forms ovate to very broadly ovate and broad elliptic to orbicular leaves having a satiny luster and a leathery texture as the 'Vegeta' variety (non-patented in the United States) which tend to be larger than those of most other *Euonymus fortunei* plants,
(b) forms distinctive wide irregular whitish-cream or sometimes cream leaf margins which surround and penetrate into marbled green and deep forest green leaf centers,
(c) forms new growth stems of greenish-white which deepen to whitish-green before becoming woody,
(d) is less profuse blooming than the 'Vegeta' variety,
(e) is slower growing and somewhat smaller in overall size at a given age than the 'Vegeta' variety while exhibiting generally the same climbing and spreading growth habit as the 'Vegeta' variety, and
(f) exhibits good winter hardiness.

Asexual reproduction of the new cultivar by cuttings at Battle Creek, Mich. beginning in 1963 has shown that the distinctive characteristics of the new cultivar are stable and are firmly fixed from one generation to another.

The new cultivar of the present invention has been named 'Duncanata Variegated Vegeta'.

BRIEF DESCRIPTION OF THE PHOTOGRAPHS

The accompanying photographs show as nearly true as it is reasonably possible to make the same in a color illustration of this character, typical specimens of the new cultivar. The illustrated plants were grown outdoors in unimproved sandy loam soil at Battle Creek, Mich.

FIG. 1 illustrates a group of supported plants of the new cultivar including the original plant that was rooted in 1963. The climbing vining growth habit is apparent. The photograph was obtained at mid-morning during May, 1994 while using natural light.

FIG. 2 illustrates a fifteen year-old unsupported plant of the new cultivar which exhibits a height of approximately 22 inches and a width of approximately 50 to 60 inches measured in the widest direction. The left-hand side of the plant is not included in the photograph and is similar in appearance to the right-hand side that is illustrated. The photograph was obtained at approximately 11:00 a.m. on Oct. 7, 1997 while using natural light.

FIG. 3 illustrates a four year-old plant of the new cultivar which had been grown for two years in the cutting bed and two years in the field. The photograph was obtained during late afternoon in May, 1996 while using natural light. Older growth, spring growth, and the characteristic pale green stems which display a whitish appearance are shown.

FIG. 4 illustrates a cluster of orange-red arils of the new cultivar on a three month-old cutting. The cutting with its capsules was removed from a plant of the oldest plant group during August, 1996 and was placed in a cutting bed of unimproved sandy loam soil. The cutting removed in November, 1996 was found to be well rooted. It was then potted and taken to a photography studio where it was photographed under strobe lighting.

DETAILED DESCRIPTION

Figure 1:
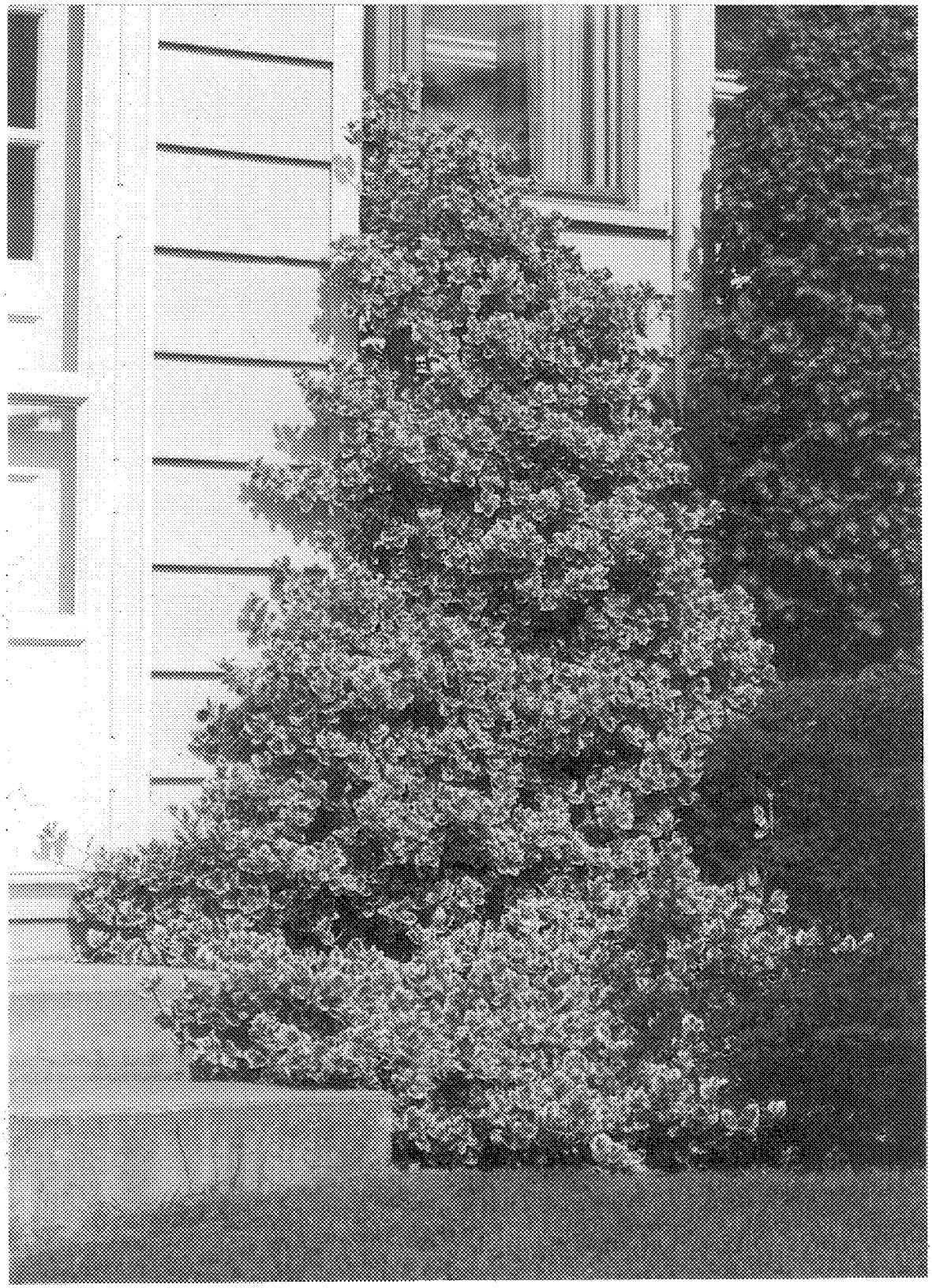
Figure 2:
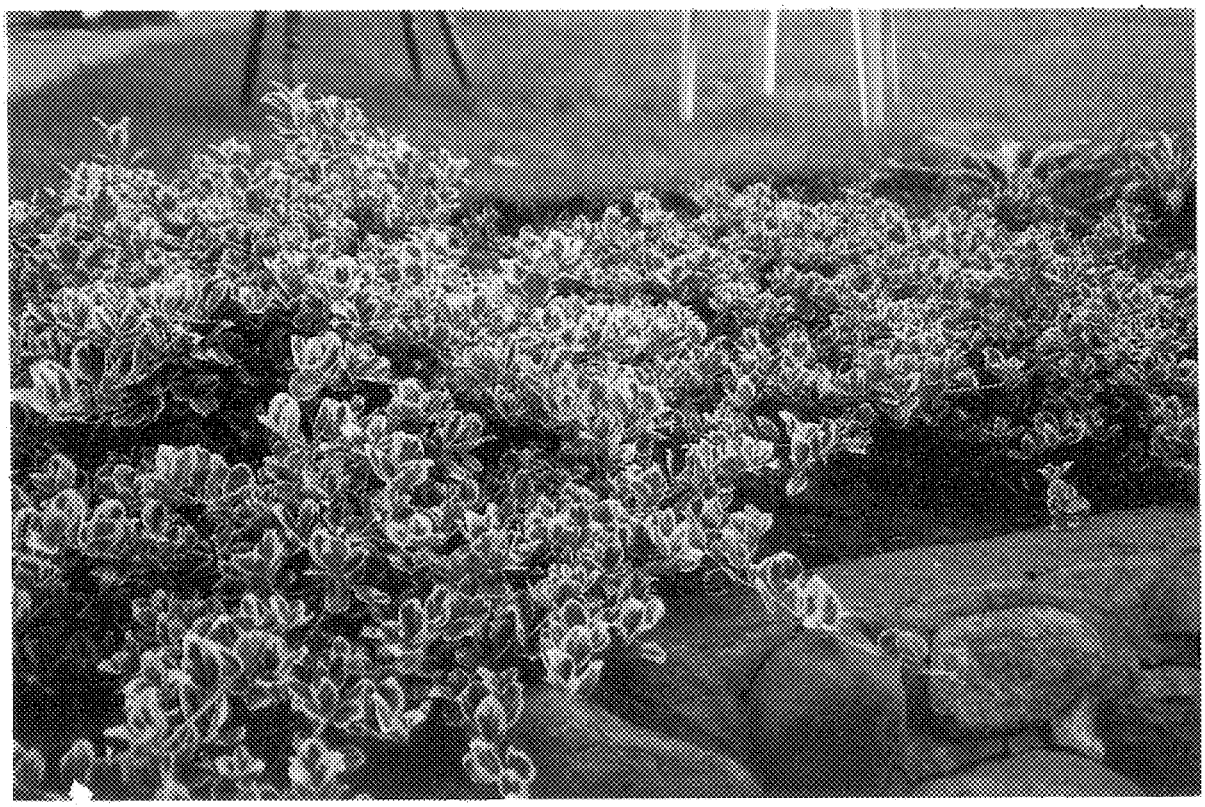
Figure 3:
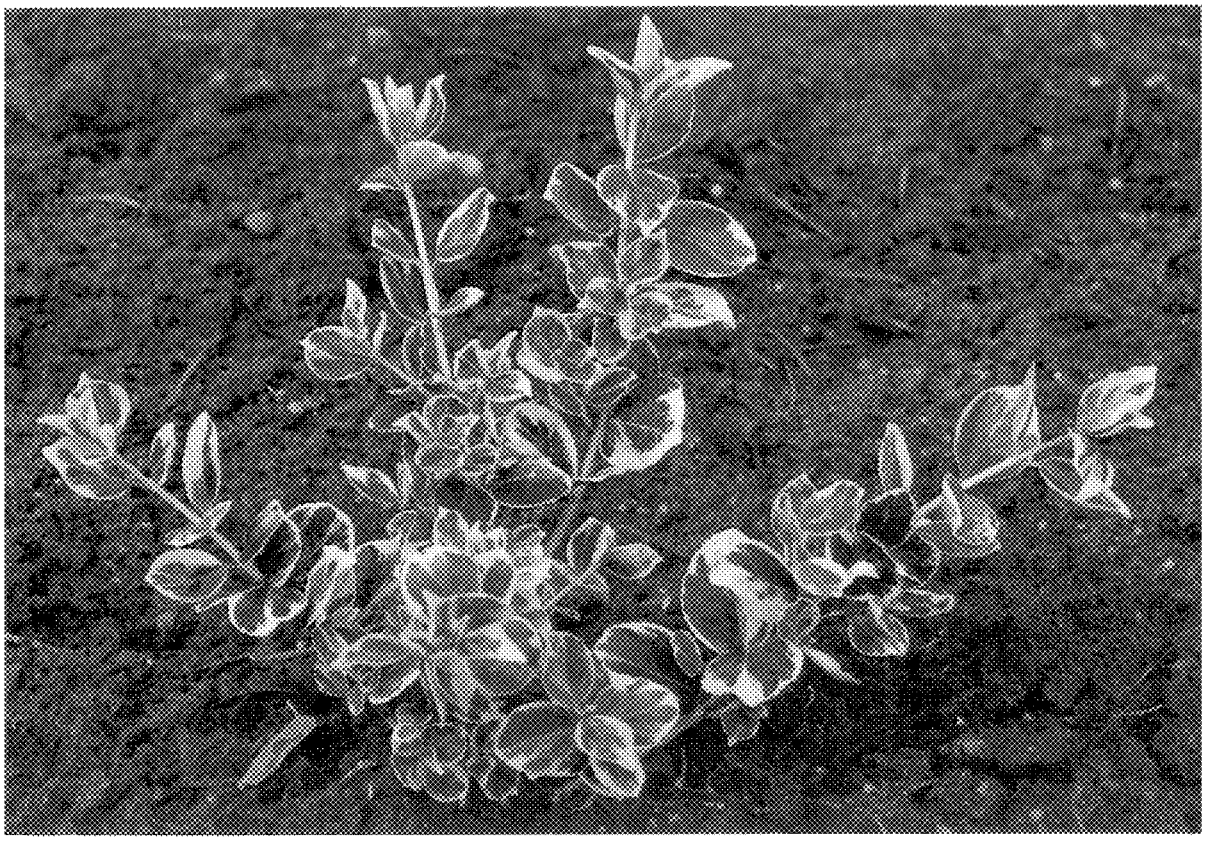
Figure 4:
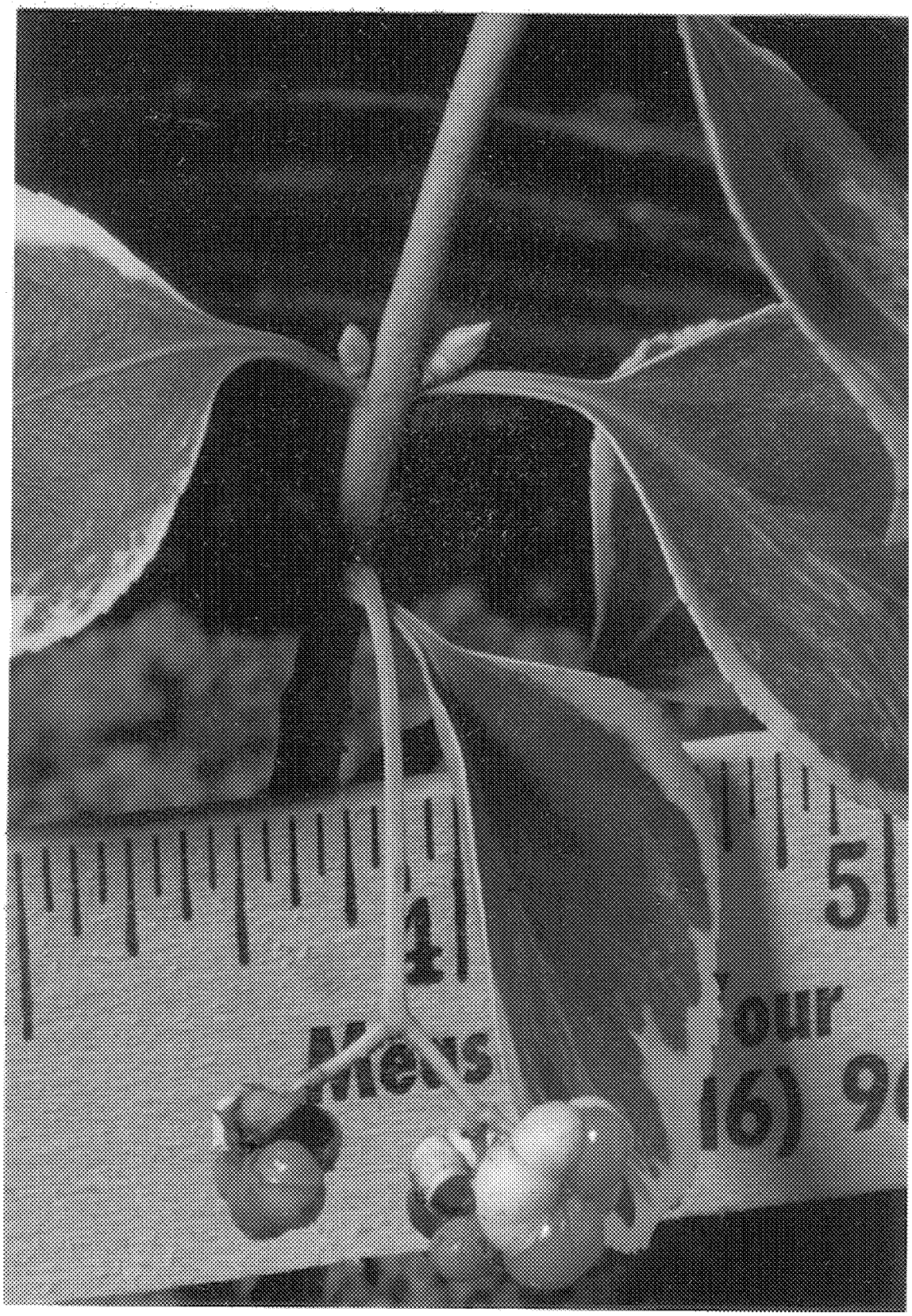

Color values were obtained with the aid of the R.H.S. Colour Chart, Royal Horticultural Society, London, except where general color terms of ordinary dictionary significance are used. Color values were taken at approximately 2 p.m. Jan. 20, 1997 and at approximately 3 p.m. on May 20, 1997 at Davie, Fla., and also at approximately 10:30 a.m. on May 27, 1997 at East Lansing, Mich., all outdoors and in the shade. A few plants had been relocated to Florida to confirm color values. These plants when expressed to a warmer climate during January were found to have a brighter, whiter margin color than what is typical for that time of year when grown in Michigan.

Form and growth habit: It has been observed that the new cultivar has approximately the same climbing or spreading form and growth habit as the parent 'Vegeta' variety with the exception that it grows somewhat less vigorously and is commonly smaller in size than a plant of the parent variety of the same age. It will grow as a self-supporting groundcover or low shrub with a spreading and bushy habit or as a clinging and climbing vine. When grown in a self-supporting form, a plant may be used as a mounding groundcover for foundation plantings, rock gardens, or low borders. An older plant may be used as a low spreading shrub which is expected to eventually reach a height of approximately 2½ feet when the side branches are pruned yearly to help the plant attain more height. When grown as the vining landscape form, the plant is expected to eventually reach a vertical height of approximately 15 feet, or more, if the leader stems find support on which branches can lean or rootlets can grasp, such as a masonry or rock wall, a fence, a trellis, or a tree. It has been observed that young leader stems which encounter such support will commonly tend to climb. Young climbers may be trained, if desired. A climbing leader stem when touching a vertical surface has been observed to grow approximately 3 feet in a single growing season with 12-12-12 fertilization and without fertilization.

*Two year plants.*—The common height of a two year old unsupported plant in the cutting bed is approximately 4 to 7 inches and a common width is approximately 3 to 6 inches.

*Five year plants.*—The common height of a five year-old unsupported plant which has been groomed annually since its second or third year is approximately 8 inches and a common width is approximately 10 to 12 inches.

*Seven year plants.*—The common height of a seven year-old unsupported shrub which has been heavily trimmed each year for the production of cuttings is approximately 10 inches and a common width is approximately 15 to 18 inches.

*Ten year plants.*—The common height of a ten year-old unsupported plant which has been heavily trimmed each year for production of cuttings is approximately between 12 and 15 inches and a common width is approximately 18 to 24 inches.

Foliage:

*Type.*—Broadleaf evergeen with petioled, opposite, and simple leaves.

*Shape.*—Does not appear to differ substantially from the parent 'Vegeta' variety. The leaves commonly are ovate to very broadly ovate, and broad elliptic to orbicular and commonly have obtuse bases, apices are often obtuse, and have a blunt tip or are rounded as the parent 'Vegeta' variety.

*Petioles.*—The length commonly is approximately 3 to 9 mm. The petiole coloration was observed to be Green Group 141B both indoors under fluorescent lighting and outdoors in full sun at approximately 2 p.m. on Oct. 23, 1998 at East Lansing, Mich.

*Size.*—Large. The leaf size commonly is larger than that of most other cultivars of *Euonymus fortunei*, and is generally comparable to that of the parent 'Vegeta' variety. It commonly is broad, as is that of the parent 'Vegeta' variety. A fully expanded leaf can vary up to approximately 4.7 cm. in length on a two to fifteen year-old plant and up to approximately 5.6 cm. in length on a plant that is more than fifteen years of age. The fully expanded leaf on a thirty-four year old plant commonly has been observed to be approximately 1.7 to 5.0 cm in length and approximately 1.2 to 3.8 cm. in width at the widest point. A fully expanded leaf on a five year-old plant that was weakened by scale has been observed to be approximately 1.7 to 4.8 cm. in length and approximately 1.2 to 2.9 cm. in width at the widest point. The smaller leaf sizes commonly occur on fast-growing leader stems.

*Leaf texture.*—Texture generally is leathery and glabrous, and the luster is satiny as are the leaves of the parent 'Vegeta' variety.

*Veining.*—The midvein commonly is raised on the bottom surface of the medium to large-sized leaves, and on the top surface of most leaves the midvein commonly is raised on the proximal one-half of the leaf. On the upper surface of a mature leaf, the midvein is grey-green across leaf areas that are of that color. This was Grey-Green Group 193A when observed outdoors in the shade on Oct. 20, 1998 at East Lansing, Mich. Where the midvein crosses green areas of the leaf, the color commonly is Greep Group 141B as observed at Davie, Fla. on Jan. 20, 1997.

*Leaf margins.*—Edges are serrate as those of the parent 'Vegeta' variety.

*Color.*—Mature leaves, upper surface: The leaves of the new cultivar are variegated unlike those of the parent 'Vegeta' variety. Such variegation commonly covers approximately 20 to 60 percent of the upper surface area with whitish coloration. This coloration is luminous whitish-cream during mild weather and slightly lighter than Yellow Group 4D at Davie, Fla. on Jan. 20, 1997. This tends to deepen slightly toward cream during the winter and was Yellow Group 10D at East Lansing, Mich. under fluorescent light on Nov. 1, 1996. This whitish-cream margin color surrounds the leaf center as an oftentimes very irregular border. It may be found reaching towards the petiole of the leaf, and penetrating into the green colors generally found at or near the leaf center. These greens are more fully described as marbled, and as rounded or elongated patches and strands of various shades of green and deep forest green. The darkest shade was observed to be slightly darker than Green Group 137A at Davie, Fla. on Jan. 20, 1997. Also, during the heat of the summer, the faster growing leader stems have been observed to occasionally form leaves with more green area and narrower whitish-cream margins than is common for this cultivar. Rarely yellowish-green coloration has appeared as a small patch or spot averaging approximately 2 to 3 mm. in size on the leaf. However, during the Fall of 1998 no such coloration has been observed. Mature leaves, under surface: On the bottom side of the mature leaf, the margin color was Yellow Group 8D at Davie, Fla. on Jan. 20, 1997. The greens of the under surface of the leaves are duller, paler, and show less contrast than those above, with the darkest shade being Green Group 138B at Davie, Fla. on Jan. 20, 1997. It has been observed that rarely some leaves assume a temporary pinkish coloration of the edges during the winter. Immature leaves, upper surface: The upper surface margin color of the slower growing new growth is commonly a pale cream which was between Yellow Group 4C and Yellow Group 8D on newly opening leaves at Davie, Fla. on May 20, 1997. The deepest green found on such leaves was commonly Green Group 143B at Davie, Fla. on May 20, 1997. However, the coloration of many newly formed young leaves in the springtime can be of a more yellow hue in both creams and greens. This stronger coloration is not a common trait in new growth during other seasons. This coloration as observed on Dec. 7, 1998 outdoors at East Lansing, Mich., was Red-Purple Group 57C near the tips of the leaves. Immature leaves, under surface: The under surface margin color of the slower-growing new growth commonly was observed to be Yellow Group 4D on newly opening leaves at Davie, Fla. on May 20, 1997. The deepest green was observed to be between Green Group 138B and 138C at Davie, Fla. on May 20, 1997. The under surface colors on faster-growing new growth, most commonly seen in the springtime and infrequently in the faster-growing new growth of other seasons, have paler greens and both greens and creams are of a somewhat more yellow hue. A short stem of small, all-whitish-cream leaves will occasionally grow from a plant of the new cultivar, as will also an occasional stem of all-green leaves.

Axillary buds: Conical, somewhat flattened and spear-shaped in fall and winter, with a length up to approximately 5 mm. on a typical four year-old plant; and conical in the springtime.

Stems: Stems that have not yet become woody have a distinctive whitish appearance, unlike those of the parent 'Vegeta' variety. They first appear as a very pale greenish-white, which was Green-White Group 157A at East Lansing, Mich. on May 27, 1997, and later become slightly more green, Yellow-Green Group 145C at East Lansing, Mich. on May 27, 1997. These stems are nearly round, have a slightly rough texture, and climb by fine masses of rootlets, as does the parent 'Vegeta' variety. Where a sprawling branch touches the ground, these rootlets may root into the soil. The leaf internode length has shown itself to range approximatley the same as that of the parent 'Vegeta' variety, most commonly varying from approximately one inch to approximately four or five inches between the nodes of faster growing climbers. A woody stem of approximately five years of age when observed outdoors at East Lansing, Mich., on Oct. 20, 1998 exhibited a coloration of Brown Group 200B.

Flowers and fruits: Blooms and fruits are less abundant than those of the parent 'Vegeta' variety. Flowers appear on both the vining form and on the self-supporting form. Healthy plants have been observed to bloom and bear fruit for the first time during its second year in the cutting bed. Flower buds first appear about mid-May and the inconspicuous flowers open about mid- to late-June in southern Michigan, as do those of the parent 'Vegeta' variety. They are a creamy color blending into pale greenish-cream centers. Flowers have been observed to occur in clusters of approximately 4 to 20 and capsules commonly occur in clusters of approximately 2 to 8. They commonly have long-peduncled cymes. Capsules and arils were observed at East Lansing, Mich. on Oct. 20, 1998. Some capsules had not yet begun to split. The capsules that had just begun to split displayed the orange-red of the underlying arils through the seams of the capsules. The capsule coloration was observed to be Yellow-White Group 158B, and the aril coloration was observed to be Orange-Red Group 30C. The seeds commonly have been found to be viable, but due to the use of open pollination, it is not known whether they are viable when self-pollinated. The dehiscence of the new variety is substantially the same as that of the parent 'Vegeta' variety.

Hardiness: Good winter hardiness has consistently been observed. No difference in hardiness when compared to the parent 'Vegeta' variety has been noted in U.S.D.A. Hardiness Zone No. 5 at Battle Creek, Mich., where it has been exposed to temperatures of below −10° F. The new cultivar has not been tested to date in colder U.S.D.A. Hardiness Zones.

Drought tolerance: The cultivar has shown good drought tolerance as has the parent 'Vegeta' variety. However, even established plants may require irrigation during extended dry periods.

Pests: The new cultivar, as the parent 'Vegeta' variety, is susceptible to serious infestations of scale and should be examined closely for such pests. All plants preferably are treated with dormant oil spray before each growing season. Also, in early spring, newly opening leaf buds and tender foliage should be examined with a hand lens for immature crawlers. For instance, crawlers have been found from early May through mid-June in southern Michigan. They have been successfully controlled with Malathion and Orthene insecticides. The new cultivar has shown some susceptibility to gall as does the parent 'Vegeta' variety. This pest has been successfully treated by cutting out and removing the diseased part, or by removing the entire plant if the roots are affected. A plant growing in U.S.D.A. Hardiness Zone No. 10 in May 1997 at Lake Worth, Fla. showed some new growth damage from mealybugs. This location is about 200 miles south of the southernmost recommended growing region. This result was surprising because plants of the new cultivar growing in Michigan have not shown vulnerability to mealybugs in over three decades of observations.

I claim:

1. A new and distinct cultivar of *Euonymus fortunei* having the following combination of characteristics:

(a) forms ovate to very broadly ovate and broad elliptic to orbicular leaves having a satiny luster and a leathery texture as the 'Vegeta' variety (non-patented in the United States) which tend to be larger than those of most other *Euonymus fortunei* plants, (b) forms distinctive wide irregular-whitish-cream or sometimes cream leaf margins which surround and penetrate into marbled green and deep forest green leaf centers, (c) forms new growth stems of greenish-white which deepen to whitish-green before becoming woody, (d) is less profuse blooming than the 'Vegeta' variety, (e) is slower growing and somewhat smaller in overall size at a given age than the 'Vegeta' variety while exhibiting generally the same climbing and spreading growth habit as the 'Vegeta' variety, and (f) exhibits good winter hardiness;

substantially as illustrated and described.

* * * * *